(12) United States Patent
Redmond et al.

(10) Patent No.: US 11,491,282 B2
(45) Date of Patent: Nov. 8, 2022

(54) ELECTRONIC ASSEMBLY INCLUDING AN ULTRASONIC TRANSDUCER

(71) Applicant: Verily Life Sciences LLC, Mountain View, CA (US)

(72) Inventors: John Redmond, San Francisco, CA (US); Adam Reich, Oakland, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 648 days.

(21) Appl. No.: 16/137,164

(22) Filed: Sep. 20, 2018

(65) Prior Publication Data

US 2019/0083715 A1 Mar. 21, 2019

Related U.S. Application Data

(60) Provisional application No. 62/561,051, filed on Sep. 20, 2017.

(51) Int. Cl.
*A61M 5/315* (2006.01)
*B06B 1/02* (2006.01)
(Continued)

(52) U.S. Cl.
CPC .......... *A61M 5/31568* (2013.01); *A61M 5/20* (2013.01); *A61M 5/31511* (2013.01);
(Continued)

(58) Field of Classification Search
CPC .......... A61M 5/31568; A61M 5/31553; A61M 5/31525; A61M 5/31533; A61M 5/31545; A61M 5/31565; A61M 5/16831; A61M 5/315; A61M 5/31551; A61M 5/31573; A61M 2205/3375; A61M 2205/0294; A61M 2205/3379; A61M 2205/50; A61M 2205/8206; A61M 2205/60; A61M 2205/33; A61M 2205/35; A61M 2205/3515; A61M 2205/3523;
(Continued)

(56) References Cited

U.S. PATENT DOCUMENTS 5,165,873 A * 11/1992 Meijer ............. A61M 5/14228
417/474
9,861,756 B1 1/2018 Krasnow et al.
(Continued)

OTHER PUBLICATIONS

U.S. Appl. No. 15/333,770, Apparatus and Methods for Tracking Administering of Medication By Medication Injection Devices, filed Oct. 25, 2016, 53 pages.

*Primary Examiner* — Kevin C Sirmons
*Assistant Examiner* — Alexandra Lalonde
(74) *Attorney, Agent, or Firm* — Christensen O'Connor Johnson Kindness PLLC (57) ABSTRACT

An electronic assembly includes a casing to conduct electricity flowing between at least some electronic components disposed within the casing. The electronic components include an ultrasonic transducer coupled to emit ultrasonic signals, and a battery to provide the electricity. A controller is coupled to the ultrasonic transducer and the battery, and the controller includes logic that when executed by the controller causes the electronic assembly to perform operations, including: instructing the ultrasonic transducer to emit the ultrasonic signals.

12 Claims, 9 Drawing Sheets

(51) Int. Cl.
    *G01F 22/00*  (2006.01)
    *A61M 5/20*   (2006.01)
    *B06B 1/06*   (2006.01)
(52) U.S. Cl.
    CPC ....... *A61M 5/31553* (2013.01); *B06B 1/0207* (2013.01); *G01F 22/00* (2013.01); *A61M 2205/0294* (2013.01); *A61M 2205/3375* (2013.01); *A61M 2205/3379* (2013.01); *A61M 2205/3561* (2013.01); *A61M 2205/50* (2013.01); *A61M 2205/8206* (2013.01); *A61M 2230/201* (2013.01); *B06B 1/06* (2013.01)
(58) Field of Classification Search
    CPC .. A61M 2205/3569; A61M 2205/3592; A61M 2205/18; A61M 2205/332; A61M 2205/3368; A61M 5/31566; A61M 5/31; A61M 5/28; A61M 5/24; A61M 5/20; A61M 5/178; A61M 5/3155; A61M 5/31546; A61M 5/002; A61M 5/1413; A61M 5/1684; A61M 5/1685; A61M 5/172; A61M 2005/2006; A61M 2205/0227; A61M 2205/82; G01F 11/027; G01F 22/00; G01F 13/00; G01F 13/006; G01F 11/025; G01F 11/021; G01F 11/00; G01F 11/006; B06B 1/0207; B06B 1/06; B06B 1/00; B06B 1/02
    See application file for complete search history.

(56) References Cited

U.S. PATENT DOCUMENTS

| | | | |
|---|---|---|---|
| 2004/0210199 A1* | 10/2004 | Atterbury | G01D 5/25 604/224 |
| 2015/0174342 A1* | 6/2015 | Mitrosky | A61M 5/31525 604/506 |
| 2015/0211905 A1* | 7/2015 | Drachmann | H04R 31/006 73/861.28 |
| 2016/0259913 A1* | 9/2016 | Yu | G16H 20/17 |
| 2017/0268915 A1* | 9/2017 | Gestner | G01N 29/44 |
| 2017/0312445 A1 | 11/2017 | Mirov et al. | |
| 2020/0405949 A1* | 12/2020 | Yigal | A61M 5/46 |
| 2021/0121635 A1* | 4/2021 | Drake | A61M 5/24 |

* cited by examiner

ELECTRONIC ASSEMBLY INCLUDING AN ULTRASONIC TRANSDUCER

REFERENCE TO RELATED APPLICATION

This application claims the benefit of U.S. Application No. 62/561,051, filed on Sep. 20, 2017, the contents of which are incorporated herein by reference.

TECHNICAL FIELD

This disclosure relates generally to drug injection and in particular, but not exclusively, relates to tracking injection quantities.

BACKGROUND INFORMATION

Measuring the quantity and recording the timing of a drug's administration is an integral part of many disease treatments. For many treatments, to achieve the best therapeutic effect, specific quantities of a drug may need to be injected at specific times of day. For example, individuals suffering from diabetes may be required to inject themselves regularly throughout the day in response to measurements of their blood glucose. The frequency and volume of insulin injections must be carefully tracked and controlled to keep the patient's blood glucose level within a healthy range.

Currently, there are a limited number of methods or devices capable of tracking drug administration without requiring the user to manually measure and record the volume, date, and time. A variety of glucose injection syringes/pens have been developed, but there is much room for significant advancement in the technology in order to reduce the size, lower the cost, enhance the functionality, and improve the accuracy. Thus, the current technology may not be an ideal long-term solution. For example, current insulin pens are often disposable, but do not include dosage tracking. A smaller portion of the market is composed of reusable pens which are more expensive, and still do not include accurate dosage-tracking capabilities.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of an apparatus and method for an electronic assembly including an ultrasonic transducer are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Packaging a very small electronics assembly for ultrasonic range-finding in medication injection devices is difficult. Spatial constraints can preclude the use of traditional approaches to make mechanical and electrical connections (connectors, soldering, spring clips, etc.). Embodiments disclosed herein provide new ways to produce miniature ultrasonic range-finding circuitry for plunger heads and other applications.

In some embodiments, an important aspect of the disclosure is the use of a can/casing to serve as a protective housing, acoustic matching layer, and electrical chassis for an ultrasonic transducer device. This provides mechanical and manufacturing benefits, eliminating the need to route any wires to the ultrasonic transducer (e.g., a piezoelectric element).

In some embodiments, the device may include a piezoelectric element and backing layer secured within a metal casing/can, and the can material has a thickness chosen to optimize acoustic signal transmission into the medium (e.g., fluid in the drug cartridge). The device may also include one or more electrical connections to piezoelectric element provided through mechanical contact with the metal can surface and/or conductive element(s) on top of the piezoelectric, achieved without soldering. This would result in a very low cost device to accurately measure dosage. The system here may also contain an integral printed circuit board assembly (PCBA) for triggering/measuring piezo response, an integral battery, and an antenna for communicating with external devices. Moreover, the system could provide time of flight measurements to calculate liquid level. These components may be installed in a rubber sleeve/plunger within a drug delivery device for measuring volume of contents, and could be assembled based upon simple insertion of components with solderless contact, secured via adhesive.

In some embodiments the electronic components discussed above could be placed in an encapsulant to form a "pill-like" ultrasonic transducer device that could be molded or mechanically inserted into a stopper. For example, the electronic devices encapsulated in the pill could then be overmolded with rubber.

The following disclosure will describe the embodiments discussed above, and other embodiments, as they relate to the figures.

Figure 1:
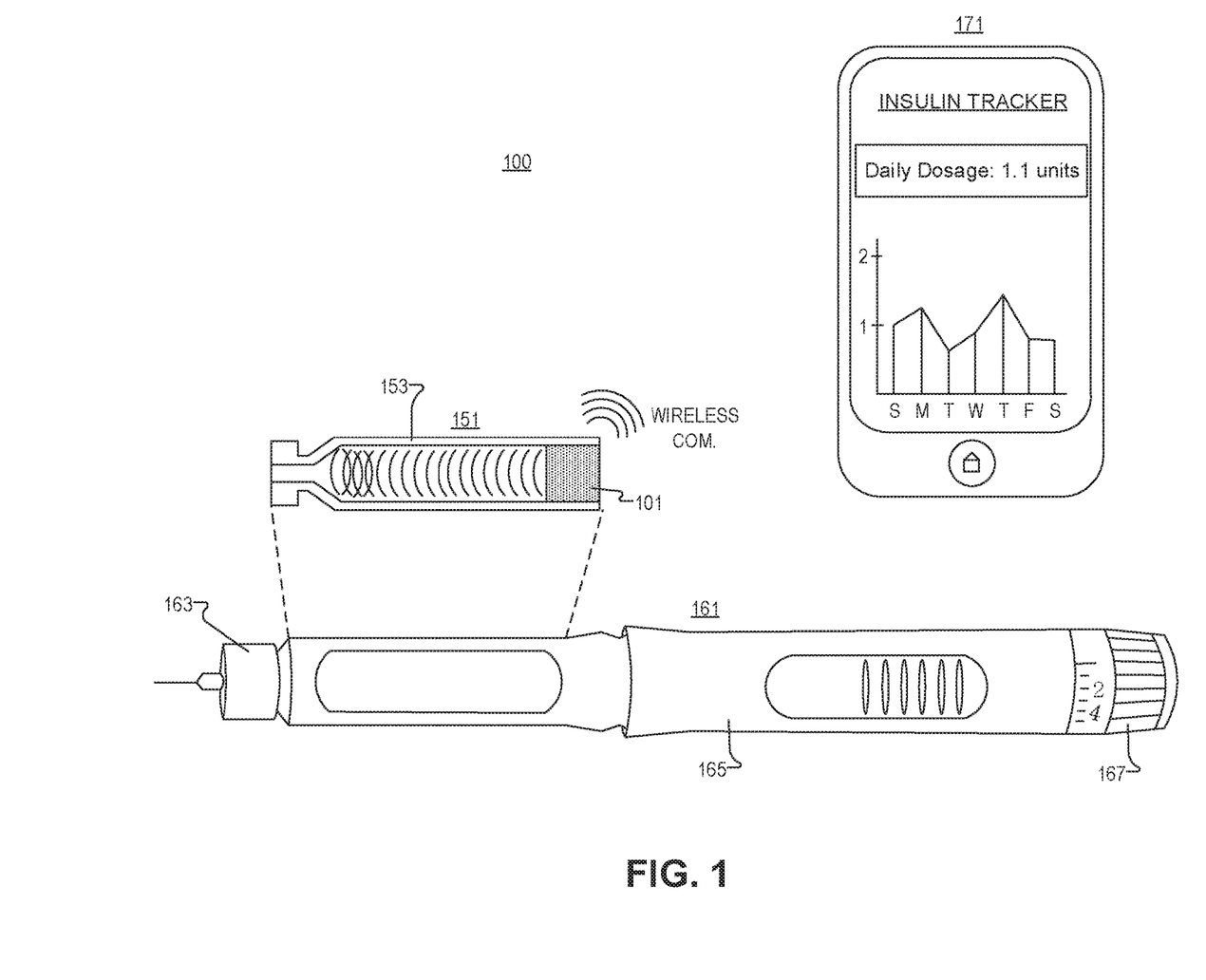
FIG. 1 illustrates an injection pen system, in accordance with an embodiment of the disclosure.

FIG. 1 illustrates an injection pen system 100, in accordance with an embodiment of the disclosure. Pen system 100 includes injection pen 161, drug cartridge 151, and processing device 171 (e.g., a smart phone).

Drug cartridge 151 includes cartridge body 153, and plunger head 101. In the depicted embodiment, plunger head 101 starts near the rear of drug cartridge 151 and is pushed forward in drug cartridge 151 (with a plunger disposed in injection pen 161). This forces medication/fluid from the narrow end of drug cartridge 151 when a user chooses to dispense a fluid. In one embodiment, cartridge body 153 includes borosilicate glass, and plunger head 101 includes an elastomer.

Although depicted in greater detail later, plunger head 101 is a "smart" plunger head that can be used to measure a quantity of fluid dispensed from drug cartridge 151. Accordingly, plunger head 101 includes an ultrasonic transducer coupled to emit ultrasonic signals (curved lines traveling away from plunger head 101) along a length of the barrel when the plunger head 101 is disposed in the barrel. The same or a different ultrasonic transducer is disposed within plunger head 101 and oriented to receive reflections of the ultrasonic signals (curved lines traveling back towards plunger head 101). The ultrasonic signals may generally travel down the barrel and back without interference in between (other than the reflection in the dispensing end of the barrel). The ultrasonic transducer(s) may be made from an actuator, piezoelectric element, speaker-like voice coils, or the like. A controller is disposed in plunger head 101 and is coupled to the ultrasonic transducer. The controller includes logic that when executed by the controller causes the controller to perform operations including instructing the ultrasonic transducer(s) to emit the ultrasonic signals.

In the depicted embodiment, the controller may calculate a time of flight for the ultrasonic signals to travel from the ultrasonic transducer in the plunger head to a dispensing end of the barrel, be reflected by the shoulder of the barrel or an insert, and be reflected back to the plunger head. In other words, the controller may determine the difference in time between the ultrasonic signal being emitted, and the ultrasonic signal being received. This time of flight (TOF) may then be used to calculate a position of the plunger head (position=TOF/(speed of sound in medium)/2). If the time of flight is correlated to the plunger head's position in the barrel, the controller can determine the amount of fluid dispensed based on the time of flight (e.g., $(P1-P2)\pi r^2$, where r is the inner radius of the barrel, and P1 and P2 are the first and second positions of the plunger head in the barrel, respectively). Accordingly, once the time of flight is known, the controller (e.g., one or more integrated circuits) may calculate a wide array of information about the fluid dispensed.

Injection pen 161 is a hand-held device and includes needle 163, body 165 (including the plunger to push in plunger head 101 and extract fluid from drug cartridge 151), and drug delivery control button 167 (twist button 167 to "click" control the dosage, press button 167 to dispense the fluid from drug cartridge 151). As shown, body 165 is configured accept drug cartridge 151. In the depicted embodiment, drug cartridge 151 may be disposed in an insert which screws/snaps onto the bulk of body 165. However, as one of ordinary skill in the art will appreciate, injection pen 161 can take other configurations and have other components.

Processing device 171 (e.g., a smartphone, tablet, general purpose computer, distributed system, servers connected to the internet, or the like) may be coupled to receive dosage data from plunger head 101 (or injection pen 161—depending on where the transmitter circuit is located) to store/analyze this data. For instance, in the depicted embodiment, processing device 171 is a smartphone, and the smartphone has an application running recording how much insulin has been spent from injection pen 161. Moreover, the application is plotting how much insulin has been injected by the user over the past week.

Figure 2:
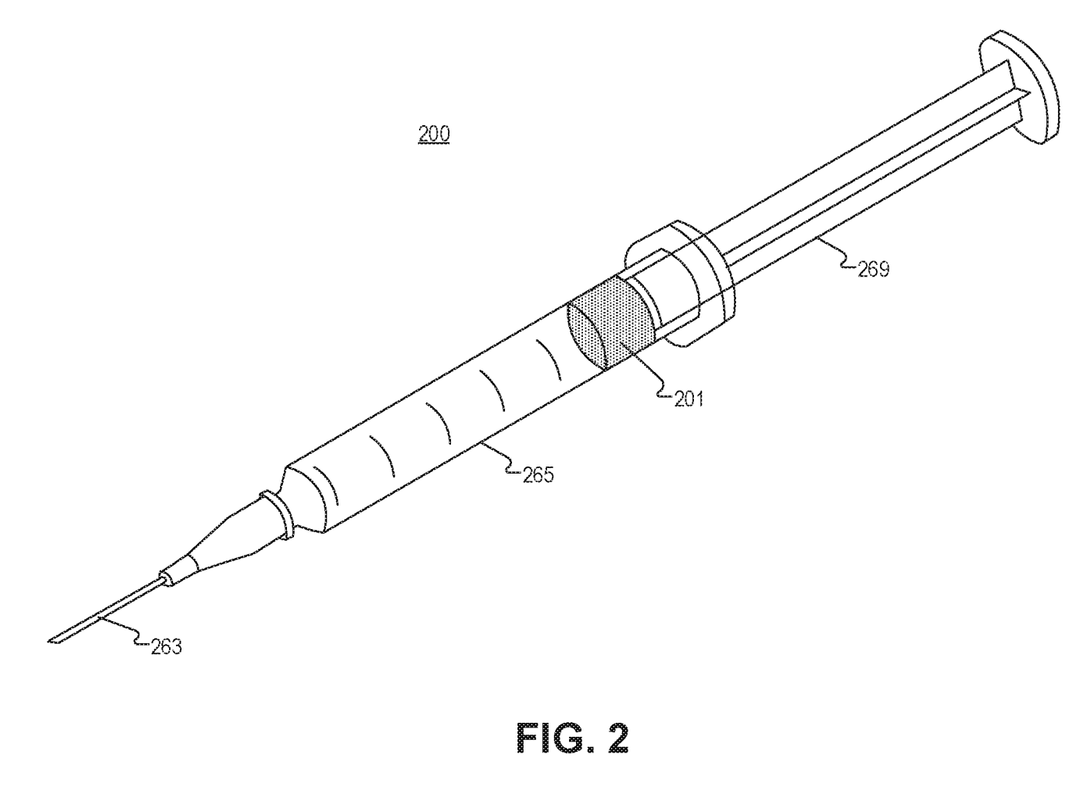
FIG. 2 illustrates a syringe system, in accordance with an embodiment of the disclosure.

FIG. 2 illustrates a syringe 200 system, in accordance with an embodiment of the disclosure. As illustrated, plunger head 201 (which may have all the same components as plunger head 101 in FIG. 1) may have been placed in body 265 of syringe 200 in order to measure dosage quantity, temperature of the medication, conductivity of the medication or the like. Plunger head 201 may be installed in a standard syringe 200 by withdrawing plunger 269, removing the standard plunger head, and installing plunger head 201. In some embodiments, syringe 200 may be manufactured and supplied with a plunger head 201 preinstalled. Plunger head 201 may be sized to correspond with the size of body 265. For example, plunger head 201 may be formed to fit any size syringe 200. Needle 263 may come preinstalled or be attached by the user. Since the shoulder region of syringe body 265 is shaped similarly to the shoulder region of a drug cartridge (e.g., drug cartridge 151 in FIG. 1), plunger head 201 can send and receive ultrasonic signals in syringe 200 in almost the same way as it can in a drug cartridge.

Figure 3A:
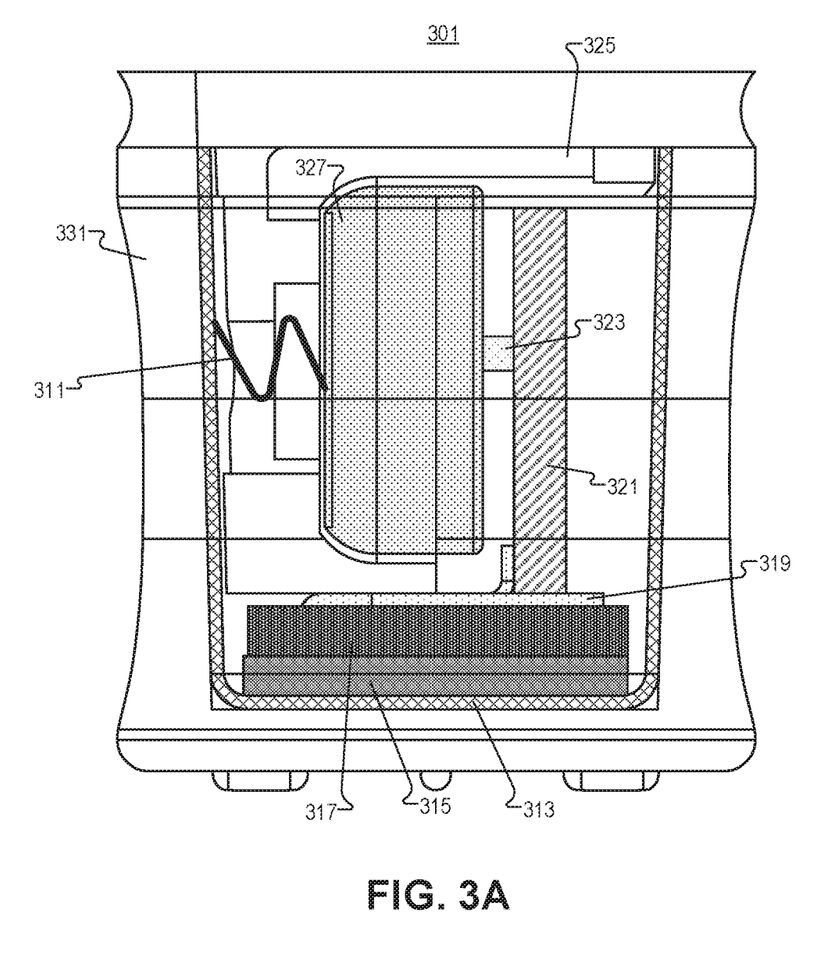
FIGS. 3A-3C illustrate an electronic assembly including an ultrasonic transducer, in accordance with an embodiment of the disclosure.
Figure 3B:
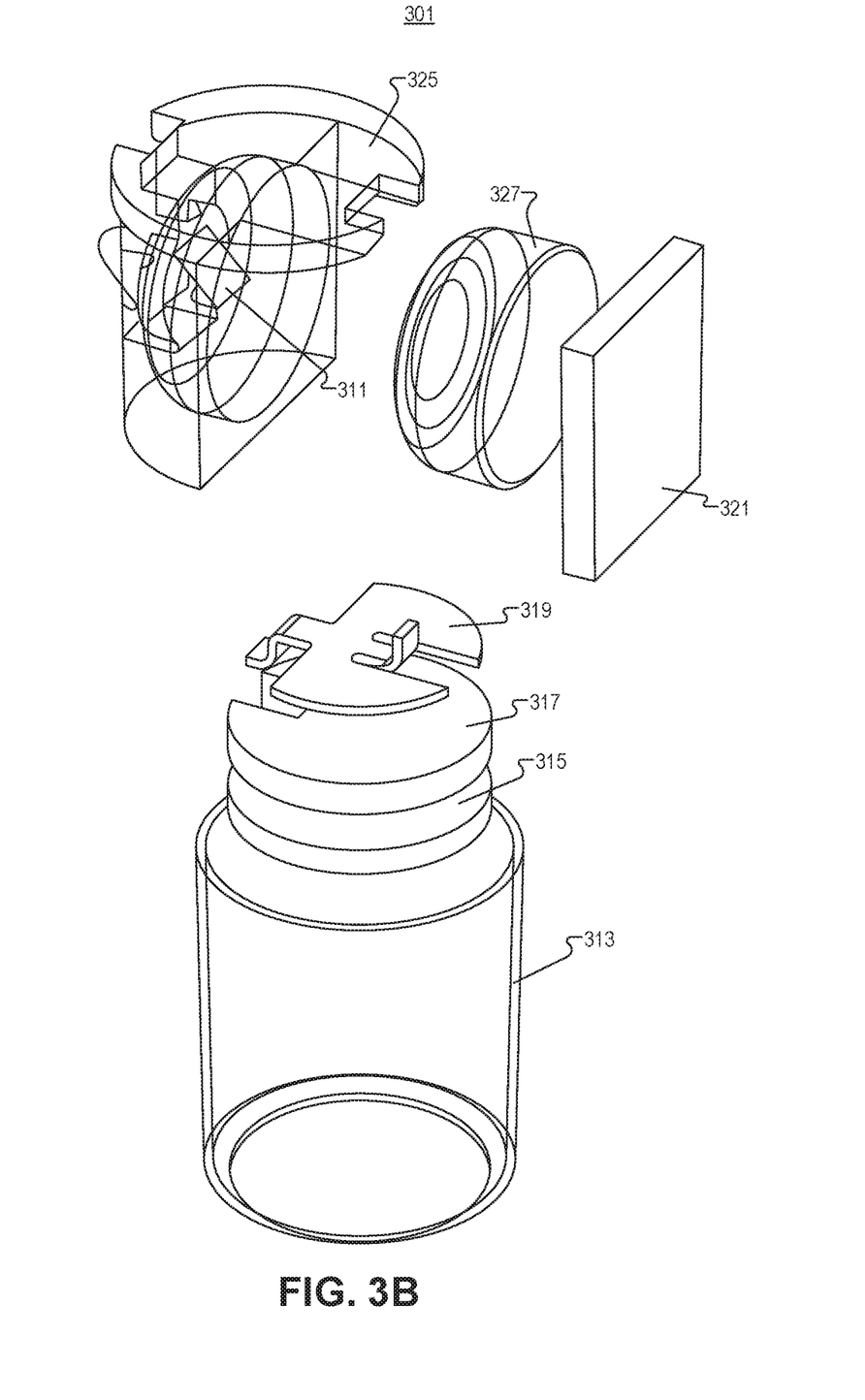
Figure 3C:
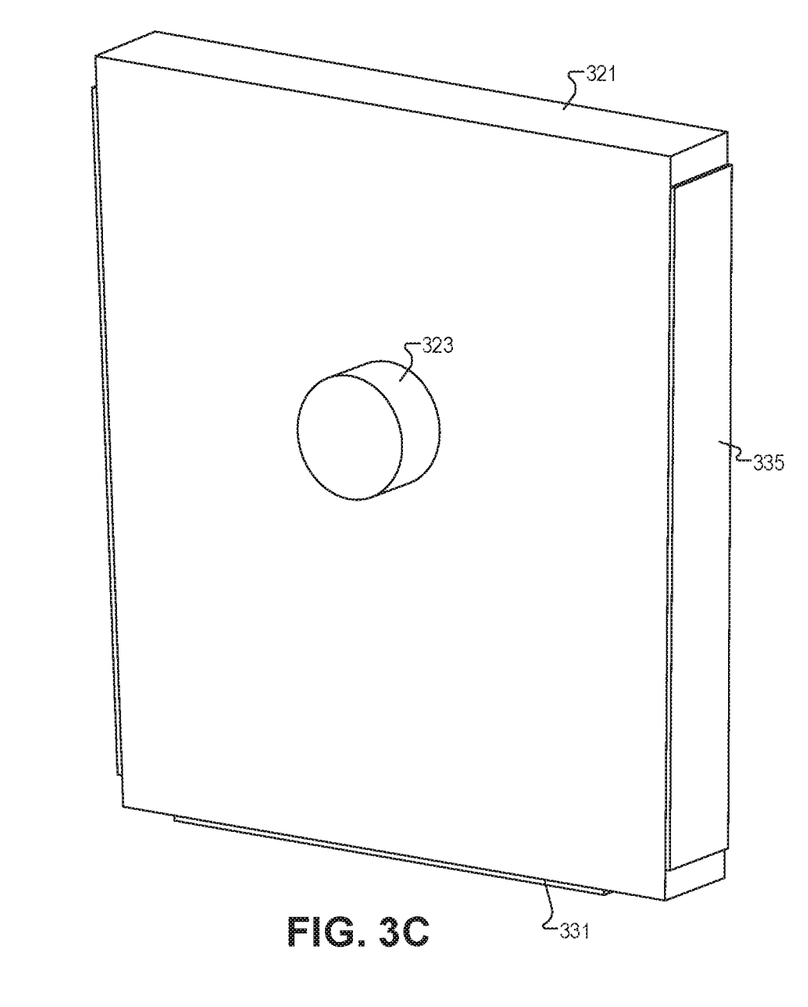

FIGS. 3A-3C illustrate an electronic assembly 301 including ultrasonic transducer 315, in accordance with an embodiment of the disclosure. The electronics assembly depicted may be included in the plunger heads shown in FIGS. 1 and 2.

FIG. 3A shows a cross section of the electronic assembly disposed in a plunger head to power and control ultrasonic transducer 315, in accordance with an embodiment of the disclosure. The electronic assembly depicted includes metal spring 311, battery holder 325, battery 327, a surface mount technology (SMT) contact 323 (here an SMT spring, SMT standoff, or SMT contact), a circuit board 321 (e.g., a printed circuit board (PCB) or printed circuit board assembly (PCBA)), metal clip 319, backing layer 317, a piezoelectric element (which may include lead zirconate titanate "PZT") ultrasonic transducer 315, a casing 313 (e.g., a metal can), and the rubber or elastomer stopper body 331. As shown, all of the aforementioned components (other than the stopper body and the metal can itself) are installed within the metal can, and all of the electronic components are electrically coupled.

A first electrode on the piezoelectric element (e.g., ultrasonic transducer 315) is in contact with, and electrically coupled to, the metal can 313. The second electrode on the piezoelectric element may be disposed on the opposite side of the crystal from the first electrode, and is electrically coupled to metal clip 319. Metal clip 319 is electrically coupled to circuit board 321, and circuit board 321 is electrically coupled to battery 321 by virtue of the SMT contact 232. Battery 327 is electrically coupled to metal can 313 by virtue of metal spring 311 (deflected and touching metal can 313 and battery 327 under compression) to complete the circuit with the piezoelectric element in ultrasonic transducer 315. Thus, the controller (e.g., ASIC, programmable processor, or the like) in circuit board 321 may send electrical signals to, and receive electrical signals from, the piezoelectric element. In other words, the controller can send electronic signals to the piezoelectric to emit the ultrasonic signals from plunger head 301 into the medication, then the piezoelectric element can receive the ultrasonic signals that were reflected from the shoulder region of the pen or syringe, and the controller can calculate the time of flight of the ultrasonic signals.

The depicted embodiment uses a unique assembly that relies on a metal can 313 enclosure (which is one embodiment of a "casing") that serves as a structural housing and an electrical connector. Using can 313 as an electrical connector is useful in space-constrained applications that do not permit the use of connectors that are typically too large to be feasible. In FIG. 3A, metal can 313 is shown to have the same voltage as the negative terminal of battery 327. However, an alternate configuration could have metal can 313 at the same voltage as the positive terminal of battery 327.

As shown, the device may utilize spring 311 that is assembled into battery holder 325 that has multiple purposes: (1) spring 311 connects the negative battery voltage to can 313; (2) spring 311 applies a lateral force on battery 327 so that it makes mechanical and electrical contact between SMT contact 323 on PCBA 321 and the positive battery terminal; and (3) the spring force presses the edges of PCBA 321 to metal can 313, making an electrical connection between the negative battery voltage and the PCBA 321 (however, in some embodiments, there may be another SMT contact on PCB 321 at this location, rather than relying on contact with the PCB edge itself). The SMT contact 323 and edge connections on the PCBA 321 are illustrated in greater detail in FIG. 3C.

Once assembled, metal can 313 enclosure is a structural element that protects the internal components until the assembly is safely installed into another structure such as a rubber stopper 313 in a medication syringe. Metal can 313 electronics assembly may be inserted into a rubber housing or a plastic stopper housing with O-ring seals. Alternatively or additionally, metal can 313 may be molded into a rubber stopper housing or a plastic stopper housing and then have the electronics assembly installed. Numerous variations and potential features of this design are considered, including having the PZT (in ultrasonic transducer 315) nominally mounted inside of metal can 313, or having the PZT mounted outside of metal can 313 (e.g., if acoustic properties of the other materials used in the system require this configuration). In one embodiment, metal can 313 may be used as a shared voltage node, e.g., as the ground plane, or V+. In one embodiment, as a space savings and assembly improving measure, connections to PCB 321 can be provided using edge plating on PCB 321 (see e.g., FIG. 3C), with PCB 321 pressed against metal can 313 to provide conductivity. In another or the same embodiment, spring clip 311 or similar can be used to maintain connectivity between connected elements, and spring clip 311 can be integral to the body of the metal can 313 (e.g., bent finger from an otherwise cylindrical shape) or attached to the battery holder 325. In one embodiment, metal can 313 may be formed via deep drawing, or assembled using an extruded or rolled tube with a separately assembled bottom. Moreover, metal can 313 may have retention tabs to support/position the bottom of the can, to support the PZT element, or to support other elements installed in metal can 313. In some embodiments, metal can 313 may serve as ground plane for a radio frequency (RF) antenna, and/or metal can 313 may include slot or interlacing features to serve as the RF antenna. One of ordinary skill in the art having the benefit of the present disclosure will understand there are multiple ways to assemble the device of FIG. 3A. Components may be substituted for other like parts; for example, metal can 313 may instead be a casing with a similar shape (made from plastic or other materials), but including electrically conductive strips disposed on the interior of the casing, in accordance with the teaching of the present disclosure.

FIG. 3B shows an exploded view of the electronic assembly 301 depicted in FIG. 3A, in accordance with an embodiment of the present disclosure. As shown, the disk-shaped piezoelectric element (which has electrodes disposed on either side and is part of ultrasonic transducer 315) is positioned between a surface of metal can 313, and backing layer 317. Backing layer 317 (e.g., butyl rubber or a tungsten-filled epoxy—tungsten powder mixed with epoxy and cured over the piezoelectric element) is disposed between the piezoelectric element and metal clip 319. Circuit board 321 and battery 323 are oriented orthogonally relative to the piezoelectric element, and are inserted into metal can 313 on top of the piezoelectric element, backing layer 317, and metal clip 319. Circuit board 321 and battery 327 are held in place with battery holder 325 which connects battery 327 to metal can 313 via metal spring 311. Battery holder 325 can be held in place by a variety of methods such as interference fit, mechanical clip, adhesive, heat-stake, etc.

FIG. 3C shows circuit board 321 and how it connects to the components depicted in FIGS. 3A and 3B, in accordance with the teachings of the present disclosure. One of ordinary skill in the art will appreciate that this is a simplified drawing of the PCB 321, as an overly complex diagram would risk obscuring certain aspects of the disclosure. A fully assembled PCB may include a controller, wireless communication circuitry (e.g., Bluetooth, RFID, etc.), charging circuitry (e.g., inductive charging rings, direct plug-ins, etc.), a clock (e.g., crystal oscillator, etc.), amplifier circuitry, digital logic, analog logic, memory (e.g., RAM, ROM, etc.), electronic packaging, and the like.

Circuit board 321 depicted here shows one possible electrode configuration including the SMT contact 323 to electrically connect the PCB 321 to the battery. Also depicted is side edge plating 335 on the PCB to electrically contact the metal can, and bottom edge plating on PCB 321 to contact the metal signal clip. Thus, PCB 321 depicted is connected to the metal clip, the metal can, and the battery when the system is fully assembled. It is appreciated that PCB 321 may be connected to additional components (e.g., an antenna) in accordance with the teachings of the present disclosure.

Figure 4A:
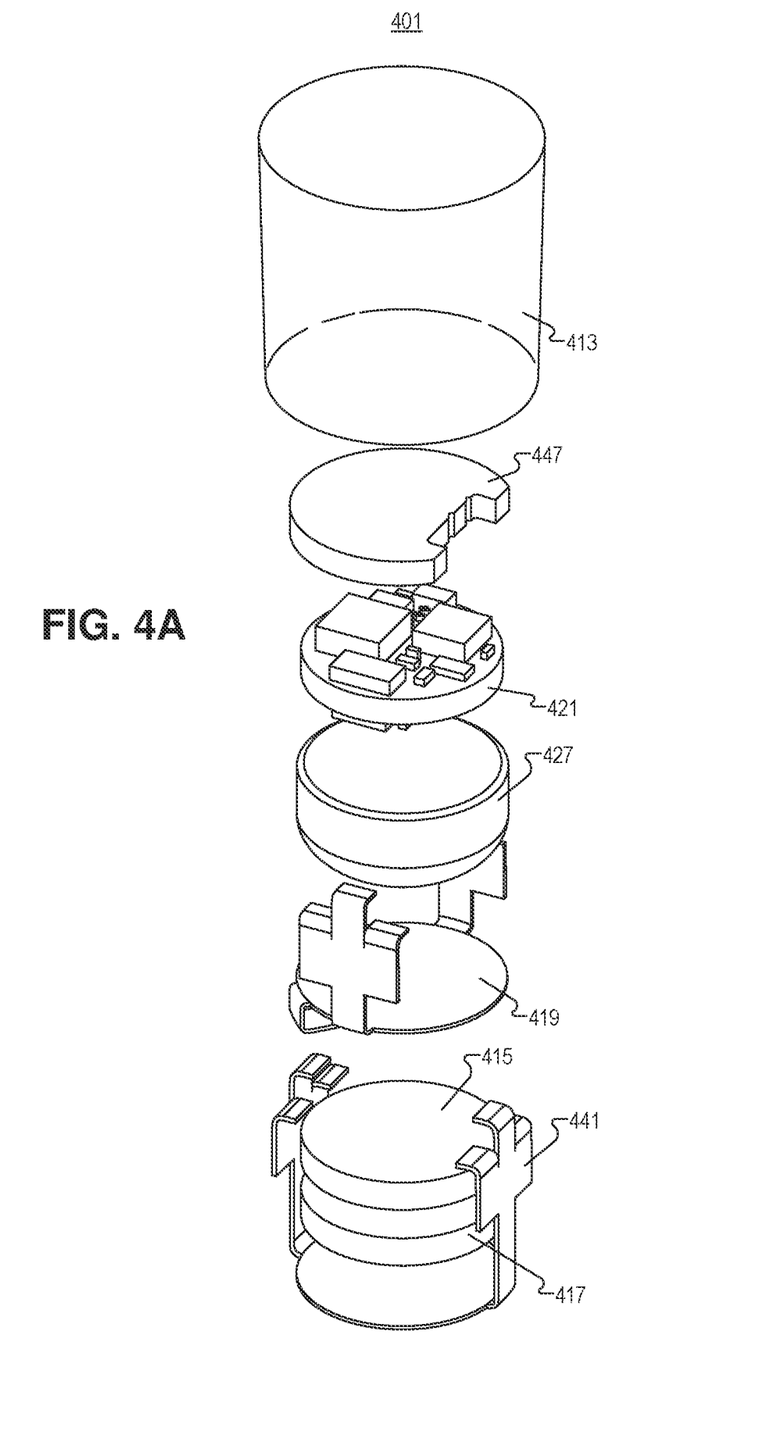
FIG. 4A illustrates an exploded view of an electronic assembly including an ultrasonic transducer, in accordance with an embodiment of the disclosure.

FIG. 4A illustrates an exploded view of an electronic assembly including an ultrasonic transducer, in accordance with an embodiment of the disclosure. Like FIGS. 3A-3C the assembly depicted may be used in the devices of FIGS. 1 and 2. Illustrated are signal clip 441, ultrasonic transducer 417, backing layer 415, metal clip 419, battery 427, circuit board 421, antenna circuit board 447, and casing 413 (e.g., an encapsulant like epoxy or the like).

The components in the electronics assembly can be configured in a variety of ways. The depicted configuration places signal clip 441, piezoelectric element (contained in ultrasonic transducer 417), backing layer 415, metal battery clip 419, battery 427, PCB 421, and antenna PCB 447 in a vertical stack, and then encapsulates the components with potting compound (e.g., epoxy, thermoplastic resin, or the like).

Voltage may need to be transmitted from electrodes on each of the circular faces of the piezoelectric element to the main PCB 421. As shown, signal clip is connects 441 the outer electrode of the piezoelectric element to the main PCB 421, and a metal battery clip 419 is shown to connect the inner face of the piezoelectric element to the main PCB 421 and the negative battery terminal. One approach would be to use a wire soldered between the outer face of the piezoelectric element and PCB 421, however the wire could create a non-flat surface, which may interfere with the ultrasound functionality. Though it is possible to obtain piezoelectric elements with both electrodes on one side, the processing cost may represent a relatively large cost increase for the component.

Here, in one embodiment, an alternative approach is proposed where signal clip 441 is aluminum. This material choice may be important because it efficiently transmits ultrasound between the piezoelectric element and the rest of the system by serving as an acoustic matching layer. However, aluminum may be difficult to solder to pads on the main PCB 421 because of an oxidized layer that quickly forms on its surface when exposed to air. To overcome this difficulty the aluminum signal clip 441 can be selectively plated with tin (or other plating materials) on part of its surface, so it may be more easily soldered to the main PCB 421. The material choice of aluminum, plating on the attachment site, and stack configuration allow the signal clip 441 to have multiple functions including structural, electrical connection between the main PCB 421 and piezoelectric element, and acoustic matching for optimized transmission of the ultrasonic signal.

Figure 4B:
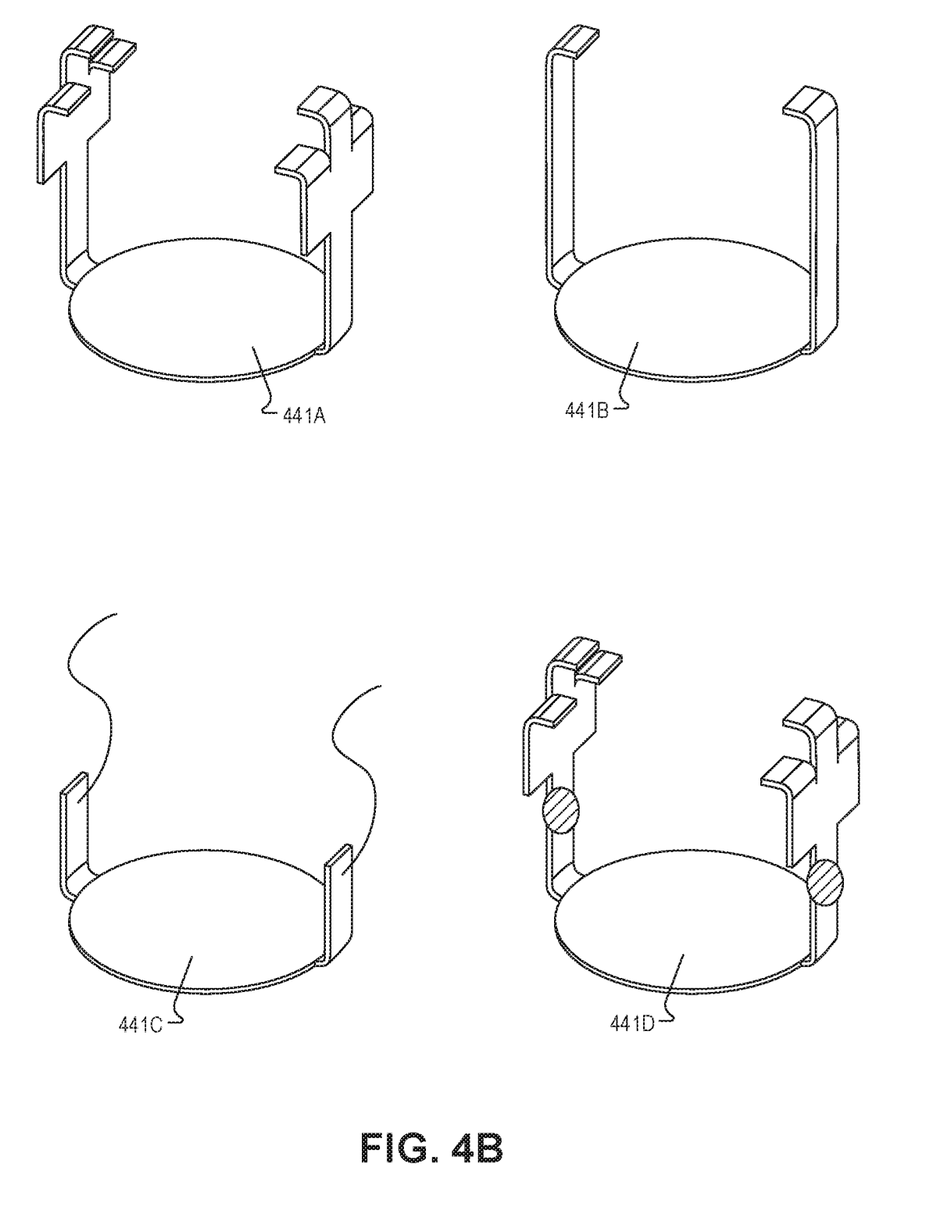
FIG. 4B illustrates a number of signal clips that can be used with the electronic assembly of FIG. 4A, in accordance with several embodiments of the disclosure.

In some embodiments (see e.g., FIG. 4B), the signal clip 441 could be aluminum on the lower surface and be crimped to wires, rods, or sheet metal clips of material that could be soldered to the main PCB, either on traditional pads on the PCB face, plated edge pads, or castellated pads on the edges. The aluminum could also be replaced with magnesium in similar clip configurations, as magnesium is a good choice for its acoustic properties. As stated, these configurations are shown in FIG. 4B. For example, embodiment 441A shows Al clip ends that are plated with Sn or other metal at the solder site. Embodiment 441B shows rods that are plated with Sn or other metal at the solder site. Embodiment 441C shows an aluminum clip with wire ends. And embodiment 441D shows an aluminum clip crimped (circle) to a solderable material.

Figure 5:
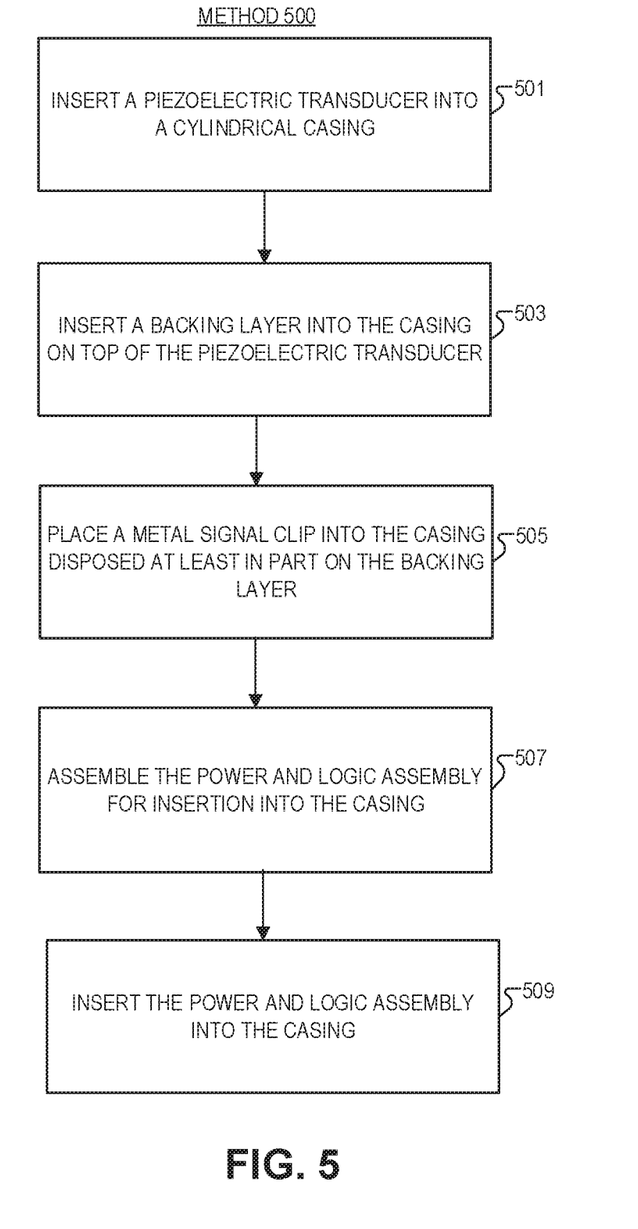
FIG. 5 illustrates a method of fabricating an electronic assembly in a plunger head, in accordance with an embodiment of the disclosure.

FIG. 5 illustrates a method 500 of fabricating an electronic assembly (e.g., the electronic assembly from FIG. 3A) in a plunger head, in accordance with an embodiment of the disclosure. The order in which some or all of process blocks 501-509 appear in method 500 should not be deemed limiting. Rather, one of ordinary skill in the art having the benefit of the present disclosure will understand that some of method 500 may be executed in a variety of orders not illustrated, or even in parallel. Further, blocks may be added to, or removed from, method 500 in accordance with the teaching of the present disclosure.

Block 501 shows inserting a piezoelectric element into a cylindrical casing (e.g., a metal can). In some embodiments, electrodes may be disposed on opposite sides of the piezoelectric material to produce the transducer. Thus, when a voltage is applied across the piezoelectric material, the piezoelectric material may expand and contract to produce an ultrasonic wave. It is appreciated that the transducer may include a speaker coil or other types of polarized crystals.

Block 503 illustrates inserting a backing layer into the casing on top of the piezoelectric element. The backing layer may mechanically dampen forces between the piezoelectric element and the metal clip (see block 405).

Block 505 describes placing a metal signal clip into the casing so that the metal clip is disposed at least in part on the backing layer. Thus the backing layer is positioned between the piezoelectric element and the metal clip. In some embodiments, the piezoelectric element, the backing layer, and the metal clip may all be sandwiched together and then inserted into the casing.

Block 507 shows assembling the power and logic assembly (including the circuit board, battery holder, and battery) for insertion into the casing. The circuit board may be a printed circuit board (e.g., PCB or PCBA, which are used interchangeably herein) and may be pressed up against the battery so that the battery is in contact with an SMT standoff on the circuit board. The battery may be inserted into the battery holder.

Block 509 illustrates inserting the battery, the printed circuit board, and the battery holder (the power and logic assembly) into the casing. The battery and printed circuit board may be oriented in the casing orthogonally relative to the ultrasonic transducer (e.g., the piezoelectric element of FIGS. 3A and 3B). The battery holder may include a metal spring which presses up against the casing (e.g., the metal can) to establish an electrical connection. Moreover, electrodes disposed on the edges of the circuit board may contact the casing.

Figure 6:
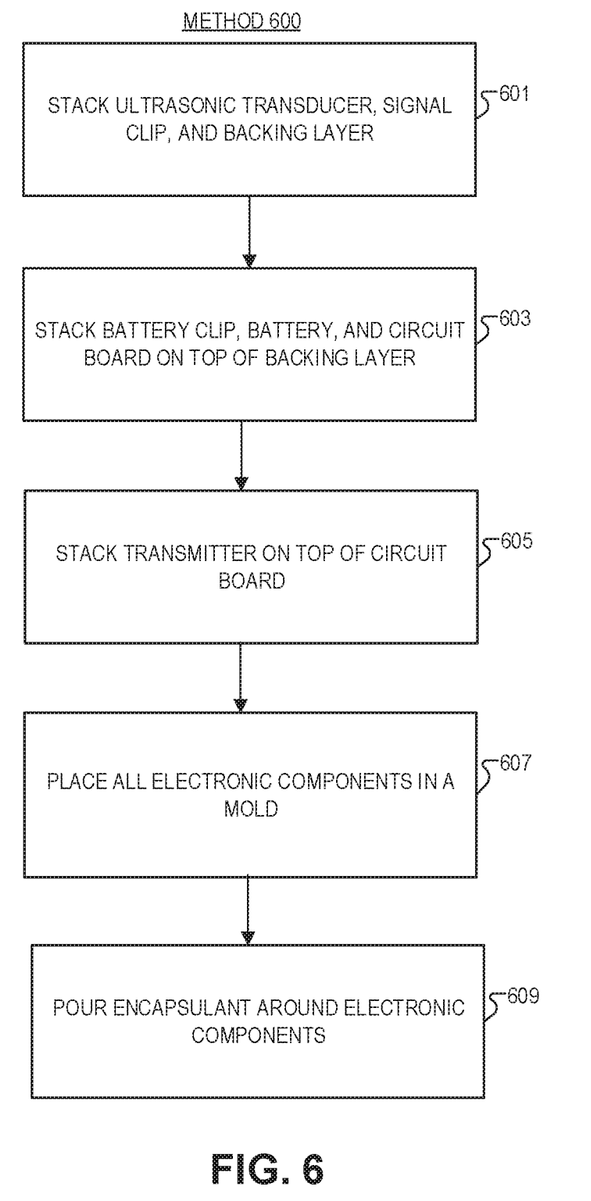
FIG. 6 illustrates a method of fabricating an electronic assembly in a plunger head, in accordance with an embodiment of the disclosure.

FIG. 6 illustrates a method 600 of fabricating an electronic assembly (e.g., the electronic assembly from FIG. 4A) in a plunger head, in accordance with an embodiment of the disclosure. The order in which some or all of process blocks 601-609 appear in method 600 should not be deemed limiting. Rather, one of ordinary skill in the art having the benefit of the present disclosure will understand that some of method 600 may be executed in a variety of orders not illustrated, or even in parallel. Further, blocks may be added to, or removed from, method 600 in accordance with the teaching of the present disclosure.

Block 601 shows stacking the ultrasonic transducer, the signal clip, and the backing layer. As shown in FIG. 4A the ultrasonic transducer may be oriented in the stack to emit ultrasonic signals, and the signal clip is electrically coupled to a first side of the ultrasonic transducer to provide power to the ultrasonic transducer. The backing layer is disposed at least in part between the battery clip (described blow) and the ultrasonic transducer to dampen vibrations between the ultrasonic transducer and the circuit board.

Block 603 illustrates stacking the battery clip, the battery, and the circuit board. The circuit board includes the controller, and the circuit board is disposed proximate to a second side, opposite the first side, of the ultrasonic transducer. The signal clip electrically couples the circuit board to the first side of the ultrasonic transducer. The battery clip is disposed at least in part between the ultrasonic transducer and the circuit board, and the battery is disposed at least in part between the battery clip and the circuit board.

Block 605 describes placing the transmitter circuit on top of the circuit board. Thus, in this step, all of the electronics depicted in FIG. 4A are fully assembled together. Accordingly, the transmitter may be used to send signals (e.g., data stored in memory coupled to, or disposed in, the controller) to external devices. Data may include dosage measurement calculations, time of flight measurements, injection time measurements, etc.

Block 607 shows placing all of the electronics in a mold. This may be done piecemeal (e.g., each electronic component is placed in the mold one by one to assemble the electronic stack) or as a completely assembled stack.

Block 609 illustrates pouring encapsulant over the electronics. Encapsulant may include epoxy or the like. Once the encapsulant dries, the encapsulated device, including all of the electronics, may resemble a hard "pill" which can be inserted or molded into a rubber stopper. In some embodiments, rather than pouring encapsulant, an overmolding technique may be used.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An electronic assembly, comprising:
   a casing including a structural housing sidewall that conducts electricity; and
   electronic components disposed within the casing, wherein the electronic components include:
     an ultrasonic transducer configured to emit ultrasonic signals, wherein the ultrasonic transducer is oriented within the electronic assembly to send the ultrasonic signals along a length of a barrel of a medication injection device when the electronic assembly is disposed in the barrel;
     a battery to provide the electricity; and
     a controller coupled to the ultrasonic transducer and the battery, wherein the controller includes logic that when executed by the controller causes the electronic assembly to perform operations, including:
       emitting the ultrasonic signals from the ultrasonic transducer,
   wherein the structural housing sidewall of the casing is electrically connected to the ultrasonic transducer and the battery to complete a circuit including at least the ultrasonic transducer and the battery such that the electricity flows through the structural housing sidewall of the casing between the battery and the ultrasonic transducer and the circuit does not include a wire directly attached to the ultrasonic transducer to complete the circuit.

2. The electronic assembly of claim 1, wherein electrical connections completing the circuit include the casing, the ultrasonic transducer, the battery, and the controller, and wherein the electrical connections are solderless.

3. The electronic assembly of claim 1, wherein the casing includes a metal can, and the ultrasonic transducer is disposed within, and electrically coupled to, the metal can.

4. The electronic assembly of claim 3, further comprising:
   a backing layer, wherein the ultrasonic transducer is disposed in the casing between the casing and the backing layer; and
   a metal clip, wherein the backing layer is disposed at least in part between the ultrasonic transducer and the metal clip to dampen vibrations between the metal clip and the ultrasonic transducer.

5. The electronic assembly of claim 4, further comprising a circuit board including the controller, and wherein the metal clip is electrically coupled to the ultrasonic transducer and the circuit board, and the circuit board is disposed in the metal can.

6. The electronic assembly of claim 5, wherein the circuit board is positioned in the metal can orthogonally relative to the ultrasonic transducer, and wherein the battery is coupled to the circuit board and the metal can.

7. The electronic assembly of claim 1, wherein the casing is hollow and cylindrical.

8. The electronic assembly of claim 1, wherein the ultrasonic transducer includes at least one of a piezoelectric material or a speaker coil.

9. The electronic assembly of claim 1, wherein the casing is installed in a rubber stopper.

10. The electronic assembly of claim 1, wherein the controller further includes logic that when executed by the controller causes the electronic assembly to perform operations, including:
    measuring a time for the ultrasonic signals to travel to an end of the barrel and return to the ultrasonic transducer when the electronic assembly is disposed in the barrel; and
    calculating a volume of fluid in the barrel based on the time.

11. An electronic assembly, comprising:
    a casing that conducts electricity; and
    electronic components disposed within the casing, wherein the electronic components include:
      an ultrasonic transducer configured to emit ultrasonic signals, wherein the ultrasonic transducer is oriented within the electronic assembly to send the ultrasonic signals along a length of a barrel of a medication injection device when the electronic assembly is disposed in the barrel;
      a battery to provide the electricity; and
      a controller coupled to the ultrasonic transducer and the battery, wherein the controller includes logic that when executed by the controller causes the electronic assembly to perform operations, including:
        emitting the ultrasonic signals from the ultrasonic transducer, wherein the casing is electrically connected to the ultrasonic transducer and the battery to complete a circuit including at least the ultrasonic transducer and the battery such that the electricity flows through a structural housing sidewall of the casing between the battery and the ultrasonic transducer and the circuit does not include a wire or a flexible conductive strip directly attached to the ultrasonic transducer.

12. The electronic assembly of claim 11, further comprising an elastomer stopper body surrounding the casing.

* * * * *